(12) United States Patent
Staas et al.

(10) Patent No.: US 8,685,965 B2
(45) Date of Patent: Apr. 1, 2014

(54) CGRP RECEPTOR ANTAGONISTS

(75) Inventors: Donnette D. Staas, Harleysville, PA (US); Ian M. Bell, Harleysville, PA (US); Harold G. Selnick, Ambler, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 103 days.

(21) Appl. No.: 13/121,784

(22) PCT Filed: Sep. 29, 2009

(86) PCT No.: PCT/US2009/058711
§ 371 (c)(1),
(2), (4) Date: May 20, 2011

(87) PCT Pub. No.: WO2010/039673
PCT Pub. Date: Apr. 8, 2010

(65) Prior Publication Data
US 2011/0224201 A1    Sep. 15, 2011

Related U.S. Application Data

(60) Provisional application No. 61/195,146, filed on Oct. 3, 2008.

(51) Int. Cl.
*A61K 31/537* (2006.01)

(52) U.S. Cl.
USPC .......................................... 514/229.5; 544/71

(58) Field of Classification Search
USPC ....................................................... 544/71
See application file for complete search history.

(56) References Cited

U.S. PATENT DOCUMENTS

| 7,625,901 | B2 | 12/2009 | Wood et al. |
| 7,629,338 | B2 | 12/2009 | Wood et al. |
| 7,893,079 | B2 | 2/2011 | Wood et al. |
| 2006/0148779 | A1 | 7/2006 | Bell et al. |
| 2007/0265225 | A1 | 11/2007 | Wood et al. |

FOREIGN PATENT DOCUMENTS

| WO | 2006029153 A2 | 3/2006 |
| WO | 2008073251 A1 | 6/2008 |

OTHER PUBLICATIONS

PCT Search Report for PCT/US2009/058711 mailed on Nov. 17, 2009, 2 pages.
Written Opinion for PCT/US2009/058711; completed on Nov. 9, 2009; 5 pages.
Supplementary European Search Report for Application No. 09818345.2-2117/2340025; completed on Apr. 12, 2012; 5 pages.

*Primary Examiner* — Brian McDowell
(74) *Attorney, Agent, or Firm* — H. Eric Fischer; John C. Todaro

(57) ABSTRACT

Compounds of Formula (I), (wherein variables $A^1, A^2, A^3, A^4, A^5, A^6, A^7, A^8, L, J, Q, R^4, E^a, E^b, E^c, R^6, R^7, R^e, R^f, R^{PG}, W, Y$ and $Z$ are as described herein) useful as antagonists of CGRP receptors, and useful in the treatment or prevention of diseases in which CGRP receptors are involved, such as headache, and in particular migraine and cluster headache. The invention is also directed to pharmaceutical compositions comprising these compounds and the use of these compounds and compositions in the prevention or treatment of such diseases in which CGRP receptors are involved.

(I)

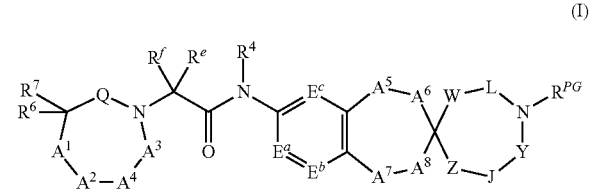

10 Claims, No Drawings

CGRP RECEPTOR ANTAGONISTS

CROSS REFERENCE TO RELATED APPLICATIONS

This application is a U.S. National Phase application under 35 U.S.C. §371 of PCT Application No. PCT/US2009/058711 filed Sep. 29, 2009, which claims priority from U.S. Provisional Application Ser. No. 61/195,146, filed Oct. 3, 2008.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), salivary levels of CGRP are elevated in migraine subjects between attacks (Bellamy et al., Headache, 2006, 46, 24-33), and CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of formula I:

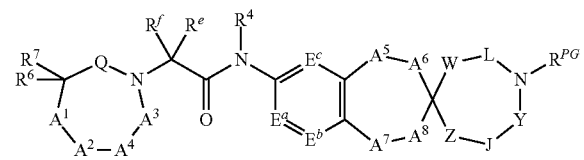

(I)

(wherein variables $A^1, A^2, A^3, A^4, A^5, A^6, A^7, A^8, L, Q, R^4, E^a, E^b, E^c, R^6, R^7, R^e, R^f, R^{PG}, W, Y$ and $Z$ are as described herein) which are antagonists of CGRP receptors and which are useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula

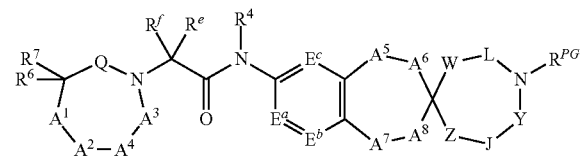

I wherein:
$A^1$ is selected from:
 (1) —O—,
 (2) —S(O)$_v$—,
 (3) —Si(OR$^a$)—C$_{1-4}$alkyl-, where alkyl is unsubstituted or substituted with 1-5 halo,
 (4) —Si(C$_{1-4}$alkyl)$_2$, where each alkyl is independently unsubstituted or substituted with 1-5 halo-,
 (5) —CR$^6$R$^7$—,
 (6) —N(R$^8$)—,
 (7) —(C=O)—,
 (8) —C(R$^8$)(R$^a$)—,
 (9) —C(N(R$^b$)—SO$_2$R$^d$)(R$^a$)—,
 (10) —C(N(R$^b$)(C=O)R$^a$)(R$^a$)—,
 (11) —C(N(R$^b$)(C=O)OR$^a$)(R$^a$)—,
 (12) —CR$^{10}$R$^{11}$—, and
 (13) —N(R$^{11}$)—;
$A^2$ is selected from:
 (1) —CR$^6$R$^7$—,
 (2) —CR$^{10}$R$^{11}$—, and
 (3) —(C=O)—;
$A^3$ is selected from:
 (1) —CR$^6$R$^7$—,
 (2) —N(R$^8$)—,
 (3) —CR$^{10}$R$^{11}$—, and
 (4) —N(R$^{11}$)—;
$A^4$ is selected from:
 (1) —CR$^6$R$^7$—,
 (2) —(C=O)—,
 (3) —N(R$^8$)—,
 (4) —CR$^{10}$R$^{11}$—,
 (5) —N(R$^{11}$)—, and
 (6) a bond between $A^2$ and $A^3$;
$A^5$ and $A^7$ are each independently selected from:
 (1) —O—,
 (2) —S(O)$_v$—,
 (3) —Si(OR$^a$)—C$_{1-4}$alkyl-, where alkyl is unsubstituted or substituted with 1-5 halo,
 (4) —Si(C$_{1-4}$alkyl)$_2$, where each alkyl is independently unsubstituted or substituted with 1-5 halo-,
 (5) —CR$^{15a}$R$^{15b}$—,
 (6) —CR$^{15a}$H,
 (7) —CH$_2$—,
 (8) —N(R$^8$)—,
 (9) —(C=O)—, and
 (10) a bond;
$A^6$ and $A^8$ are independently selected from:
 (1) —O—,
 (2) —S(O)$_v$—,
 (3) —Si(OR$^a$)—C$_{1-4}$alkyl-, where alkyl is unsubstituted or substituted with 1-5 halo,
 (4) —Si(C$_{1-4}$alkyl)$_2$, where each alkyl is independently unsubstituted or substituted with 1-5 halo-,
 (5) —CR$^{15a}$R$^{15b}$—,
 (6) —CR$^{15a}$H,
 (7) —CH$_2$—,
 (8) —N(R$^8$)—, and
 (9) —(C=O)—;
$E^a$, $E^b$ and $E^c$ are each independently selected from:
 (1) —C(R$^5$)=,
 (2) —N=, and
 (3) —(N$^+$—O$^-$)=;
or wherein $E^c$ is selected from:
 (1) —C(R$^5$)=,
 (2) —N=, and
 (3) —(N$^+$—O$^-$)=,
and -E$^a$=E$^b$- taken together are selected from:
 (1) —S—,
 (2) —O—,
 (3) —N(R$^8$)—;
L is selected from:
 (1) —C(=O)—,
 (2) —C(=S)—,
 (3) —SO$_2$—,
 (4) —SO—, and
 (5) —CR$^g$R$^h$—;
Q is selected from:
 (1) —(C=O)—,
 (2) —SO$_2$—,
 (3) —SO—, and
 (4) —C(R$^a$)$_2$—;
R$^4$ is selected from:
 (1) hydrogen,
 (2) —C$_{1-6}$alkyl, which is unsubstituted or substituted with 1-5 substituents each independently selected from:
  (a) halo,
  (b) —C$_{3-6}$cycloalkyl,
  (c) —CF$_3$, and
  (d) —O—R$^a$,
 (3) —C$_{3-6}$cycloalkyl,
 (4) benzyl, and
 (5) phenyl;

$R^5$ is selected from:
  (1) hydrogen,
  (2) —$C_{1-6}$alkyl, which is unsubstituted or substituted with 1-6 halo,
  (3) halo,
  (4) —$OR^a$, and
  (5) —CN;
$R^6$ and $R^7$ are each independently selected from:
  (1) hydrogen,
  (2) —$C_{1-6}$alkyl, which is unsubstituted or substituted with 1-5 substituents each independently selected from:
    (a) halo,
    (b) —$OR^a$,
    (c) —$C_{3-6}$cycloalkyl,
    (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl, indolyl, indazolyl, benzimidazolyl, and oxazolyl, which phenyl or heterocycle is unsubstituted or substituted with 1-5 substituents each independently selected from:
      (i) halo,
      (ii) —$C_{1-6}$alkyl, which is unsubstituted or substituted with 1-5 halo,
      (iii) —$OR^a$,
      (iv) —$NR^bR^c$,
      (v) —CN, and
      (vi) oxo;
    (e) $CO_2R^a$,
    (f) —C(=O)$NR^bR^c$,
    (g) —S(O)$_vR^d$,
    (h) —CN,
    (i) —$NR^bR^c$,
    (j) —N($R^b$)C(=O)$R^a$,
    (k) —N($R^b$)$SO_2R^d$,
    (l) —$CF_3$,
    (m) —O—$CO_2R^d$,
    (n) —O—(C=O)—$NR^bR^c$,
    (o) —$NR^b$—(C=O)—$NR^bR^c$, and
    (p) —C(=O)$R^a$,
  (3) —$C_{3-8}$cycloalkyl, which is unsubstituted or substituted with 1-5 substituents each independently selected from:
    (a) halo,
    (b) —CN,
    (c) —$C_{1-4}$alkyl, which is unsubstituted or substituted with 1-3 halo, and
    (d) —$OR^a$,
  (4) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
    (a) halo,
    (b) —$OR^a$,
    (c) —$C_{3-6}$cycloalkyl,
    (d) phenyl, which is unsubstituted or substituted with 1-5 substituents each independently selected from:
      (i) halo,
      (ii) which is unsubstituted or substituted with 1-6 halo, and
      (iii) —$OR^a$,
    (e) —$CO_2R^a$,
    (f) —C(=O)$NR^bR^c$,
    (g) —S(O)$_vR^d$,
    (h) —CN,
    (i) —$NR^bR^c$,
    (j) —N($R^b$)C(=O)$R^a$,
    (k) —N($R^b$)$SO_2R^d$,
    (l) —O—$CO_2R^d$,
    (m) —O—(C=O)—$NR^bR^c$,
    (n) —$NR^b$—(C=O)—$NR^bR^c$,
    (o) —C(=O)$R^a$,
    (p) —$C_{1-6}$alkyl, which is unsubstituted or substituted with 1-6 halo, and oxo;
  (5) halo,
  (6) —$OR^a$,
  (7) —CN,
  (8) —$CO_2R^a$,
  (9) —N($R^b$)C(=O)$R^a$,
  (10) —$NR^bR^c$,
  (11) —C(=O)$NR^bR^c$, and
  (12) —O(C=O)$R^a$,
or $R^6$ and $R^7$ and the carbon atom to which they are attached join to form a ring selected from cyclopropyl, cyclobutyl, cyclopentyl, cyclohexyl, cycloheptyl, cyclooctyl, cyclononyl, cyclobutenyl, cycloheptenyl, cyclohexenyl, cycloheptenyl, cyclooctenyl, dioxolanyl, dioxanyl, indanyl, aziridinyl, azetidinyl, pyrrolidinyl, piperidinyl, piperazinyl, morpholinyl, tetrahydrofuranyl, tetrahydropyranyl, tetrahydrothiapyranyl, oxetanyl, thietanyl and tetrahydrothienyl, wherein the sulfur is optionally oxidized to the sulfone or sulfoxide, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii)
    (iii) —$C_{3-6}$cycloalkyl,
    (iv) —$CO_2R^a$,
    (v) —$NR^bR^c$,
    (vi) —S(O)$_vR^d$,
    (vii) —C(=O)$NR^bR^c$, and
    (viii) phenyl,
  (b) —$C_{3-6}$cycloalkyl, wherein the $C_{3-6}$cycloalkyl group is optionally fused to the ring, and which $C_{3-6}$cycloalkyl group is unsubstituted or substituted with 1-3 substituents each independently selected from:
    (i) halo,
    (ii) —$OR^a$,
    (iii) —$C_{3-6}$cycloalkyl,
    (iv) —$CO_2R^a$,
    (v) —$NR^bR^c$,
    (vi) —S(O)$_vR^d$,
    (vii) —C(=O)$NR^bR^c$, and
    (viii) phenyl,
  (c) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, imidazolyl, furanyl, tetrahydrofuranyl, thiazolyl and oxazolyl, wherein the phenyl or heterocycle is optionally fused to the ring, and which phenyl or heterocycle is unsubstituted or substituted with 1-5 substituents each independently selected from:
    (i) halo,
    (ii) —$C_{1-6}$alkyl, which is unsubstituted or substituted with 1-5 halo,
    (iii) —$OR^a$,
    (iv) —$CO_2R^a$,
    (v) —O(C=O)$R^a$,
    (vi) —CN, (vii) —NR$^b$R$^c$,
(viii) oxo,
(ix) —C(=O)NR$^b$R$^c$,
(x) —N(R$^b$)C(=O)R$^a$,
(xi) —N(R$^b$)CO$_2$R$^a$,
(xii) —O(C=O)NR$^b$R$^c$, and
(xiii) —S(O)$_v$R$^d$,
(d) —OR$^a$,
(e) —CO$_2$R$^a$,
(f) —C(=O)NR$^b$R$^c$,
(g) —S(O)$_v$R$^d$,
(h) —CN,
(i) halo,
(j) —NR$^b$R$^c$,
(k) —N(R$^b$)C(=O)R$^a$,
(l) —N(R$^b$)SO$_2$R$^d$,
(m) —O—CO$_2$R$^d$,
(n) —O—(C=O)—NR$^b$R$^c$,
(o) —NR$^b$—(C=O)—NR$^b$R$^c$,
(p) —C(=O)R$^a$, and
(q) oxo;

R$^8$ is independently selected from:
(1) hydrogen,
(2) —C(=O)R$^a$,
(3) —CO$_2$R$^a$,
(4) —S(=O)R$^d$,
(5) —SO$_2$R$^d$,
(6) —C(=O)NR$^b$R$^c$,
(7) —C$_{1-6}$alkyl, which is unsubstituted or substituted with 1-5 substituents each independently selected from:
  (a) halo,
  (b) —OR$^a$,
  (c) —C$_{3-6}$cycloalkyl,
  (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
    (i) halo,
    (ii) which is unsubstituted or substituted with 1-5 halo, and
    (iii) —OR$^a$,
    (iv) —NR$^b$R$^c$,
    (v) —C(=O)R$^a$,
    (vi) —CO$_2$R$^a$, and
    (vii) oxo,
  (e) —CO$_2$R$^a$,
  (f) —C(=O)NR$^b$R$^c$,
  (g) —S(O)$_v$R$^d$,
  (h) —CN,
  (i) —NR$^b$R$^c$,
  (j) —N(R$^b$)C(=O)R$^a$,
  (k) —N(R$^b$)SO$_2$R$^d$,
  (l) —CF$_3$,
  (m) —O—CO$_2$R$^d$,
  (n) —O—(C=O)—NR$^b$R$^c$,
  (o) —NR$^b$—(C=O)—NR$^b$R$^c$, and
  (p) —C(=O)R$^a$,
(8) —C$_{3-6}$cycloalkyl, which is unsubstituted or substituted with 1-6 substituents each independently selected from:
  (a) halo,
  (b) —CN,
  (c) —OR$^a$, and
  (d) C$_{1-6}$alkyl, which is unsubstituted or substituted with 1-6 halo, or R$^7$ and R$^8$ and the atoms to which they are attached join to form a 4-, 5-, 6- or 7-membered alkyl- or heteroalkyl-ring optionally containing an additional heteroatom selected from N, O, and S, wherein the sulfur is optionally oxidized to the sulfone or sulfoxide, which ring is unsubstituted or substituted with 1-4 substituents each independently selected from:
(a) halo,
(b) phenyl, which is unsubstituted or substituted with 1-3 substituents each independently selected from: halo, OR$^a$, CN, and —C(=O)OR$^a$,
(c) —OR$^a$, and
(d) —C$_{1-6}$alkyl, which is unsubstituted or substituted with 1-6 halo;

R$^{10}$ is independently selected from:
(1) hydrogen,
(2) —C$_{1-6}$alkyl, which is unsubstituted or substituted with 1-5 substituents each independently selected from:
  (a) halo,
  (b) —OR$^a$,
  (c) —CN,
  (d) phenyl, and
  (e) —C$_{3-6}$cycloalkyl, which is unsubstituted or substituted with 1-6 halo,
(3) —C$_{3-6}$cycloalkyl, which is unsubstituted or substituted with 1-6 halo;

R$^{11}$ is independently selected from the group consisting of:
phenyl, naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, 1,3-benzodioxolyl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrralzdinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiapyranyl, and thietanyl, where R$^{11}$ is unsubstituted or substituted with 1-5 substituents each independently selected from R$^{12}$, R$^{13}$, R$^{14}$, R$^{15a}$ and R$^{15b}$;

R$^{12}$, R$^{13}$, R$^{14}$, R$^{15a}$ and R$^{15b}$ are each independently selected from:
(1) —C$_{1-6}$alkyl, which is unsubstituted or substituted with 1-5 substituents each independently selected from:
  (a) halo,
  (b) —OR$^a$,
  (c) —C$_{3-6}$cycloalkyl,
  (d) phenyl or heterocycle, wherein said heterocycle is selected from: pyridyl, pyrimidinyl, pyrazinyl, pyridazinyl, piperdinyl, piperazinyl, pyrrolidinyl, thienyl, morpholinyl, thiazolyl and oxazolyl, which phenyl or heterocycle is unsubstituted or substituted with 1-5 substituents each independently selected from:
(i) halo,
(ii) —$C_{1-6}$alkyl, which is unsubstituted or substituted with 1-5 halo, and
(iii) —OR$^a$,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —CF$_3$,
(m) —O—CO$_2$R$^d$,
(n) —O—(C=O)—NR$^b$R$^c$,
(o) —NR$^b$—(C=O)—NR$^b$R$^c$, and
(p) —C(=O)R$^a$,
(2) —$C_{1-6}$cycloalkyl, which is unsubstituted or substituted with 1-5 substituents each independently selected from:
(a) halo,
(b) —CN,
(c) —$C_{1-6}$alkyl, which is unsubstituted or substituted with 1-5 halo,
(d) —OR$^a$, and
(e) phenyl, which is unsubstituted or substituted with 1-5 substituents where the substituents are each independently selected from:
(i) —OR$^a$,
(ii) halo,
(iii) —CN, and
(iv) —$C_{1-6}$alkyl, which is unsubstituted or substituted with 1-5 halo,
(3) phenyl or heterocycle, wherein said heterocycle is selected from: pyridyl, pyrimidinyl, pyrazinyl, pyridazinyl, piperdinyl, piperazinyl, pyrrolidinyl, thienyl, morpholinyl, thiazolyl and oxazolyl, which phenyl or heterocycle is unsubstituted or substituted with 1-5 substituents each independently selected from:
(a) halo,
(b) —OR$^a$,
(c) —$C_{3-6}$cycloalkyl,
(d) phenyl, which is unsubstituted or substituted with 1-5 substituents each independently selected from:
(i) halo,
(ii) —$C_{1-6}$alkyl, which is unsubstituted or substituted with 1-6 halo, and
(iii) —OR$^a$,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —O—CO$_2$R$^d$,
(m) —O—(C=O)—NR$^b$R$^c$,
(n) —NR$^b$—(C=O)—NR$^b$R$^c$,
(o) —C(=O)R$^a$, and
(p) —$C_{1-6}$alkyl, which is unsubstituted or substituted with 1-6 halo,
(4) halo,
(5) oxo,
(6) —OR$^a$,
(7) —CN,
(8) —CO$_2$R$^a$,
(9) —C(=O)R$^a$,
(10) —NR$^b$R$^c$,
(11) —S(O)$_v$R$^d$,
(12) —C(=O)NR$^b$R$^c$,
(13) —O—CO$_2$R$^d$,
(14) —N(R$^b$)CO$_2$R$^d$,
(15) —O—(C=O)—NR$^b$R$^c$,
(16) —NR$^b$—(C=O)—NR$^b$R$^c$,
(17) —SO$_2$NR$^b$R$^c$,
(18) —N(R$^b$)SO$_2$R$^d$,
or R$^{15a}$ and R$^{15b}$ and the atom(s) to which they are attached join to form a ring selected from cyclopropyl, cyclobutyl, cyclopentyl, cyclohexyl, cycloheptyl, aziridinyl, azetidinyl, pyrrolidinyl, piperidinyl, piperazinyl, morpholinyl, thietanyl and tetrahydrothienyl, wherein the sulfur is optionally oxidized to the sulfone or sulfoxide, which ring is unsubstituted or substituted with 1-5 substituents each independently selected from:
(a) —$C_{1-6}$alkyl, which is unsubstituted or substituted with 1-3 substituents each independently selected from:
(i) halo,
(ii) —OR$^a$,
(iii) —$C_{3-6}$cycloalkyl,
(iv) —CO$_2$R$^a$,
(v) —NR$^b$R$^c$,
(vi) —S(O)$_v$R$^d$,
(vii) —C(=O)NR$^b$R$^c$, and
(viii) phenyl,
(b) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
(i) halo,
(ii) —$C_{1-6}$alkyl, which is unsubstituted or substituted with 1-5 halo, and
(iii) —OR$^a$,
(c) —OR$^a$,
(d) halo,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —O—CO$_2$R$^d$,
(m) —O—(C=O)—NR$^b$R$^c$,
(n) —NR$^b$—(C=O)—NR$^b$R$^c$, and
(o) —C(=O)R$^a$;
R$^{PG}$ is independently selected from:
(1) hydrogen,
(2) —$C_{1-6}$alkyl which is unsubstituted or substituted with 1-5 halo,
(3) —CH$_2$OR$^a$,
(4) —CH$_2$—O—CH$_2$CH$_2$Si(CH$_3$)$_3$,
(5) —CH$_2$OP(=O)(OR$^c$)$_2$,
(6) —(CH$_2$)$_k$-phenyl, which is unsubstituted or substituted with 1-3 substituents each independently selected from:
(a) halo,
(b) —OR$^a$,
(c) —CN, and
(d) —$C_{1-6}$alkyl, which is unsubstituted or substituted with 1-6 halo;

J is independently selected from:
- (1) =C($R^{16a}$)—,
- (2) —C$R^{17}R^{18}$—,
- (3) —C(=O)—,
- (4) —C(=S)—,
- (5) =N—, and
- (6) —N($R^b$)—;

Y is independently selected from:
- (1) =C($R^{16b}$)—,
- (2) —C$R^{17}R^{18}$—,
- (3) —C(=O)—,
- (4) —C(=S)—,
- (5) =N—, and
- (6) —N($R^{16b}$)—;

W is independently selected from:
- (1) a bond,
- (2) —O—,
- (3) —S—,
- (4) —N$R^a$—, and
- (5) —C$R^gR^h$—;

Z is independently selected from:
- (1) a bond,
- (2) —O—,
- (3) —S(O)$_y$—, and
- (4) —C$R^{17}R^{18}$—, wherein when W and Z are both selected to be a bond and J is selected from:
- (1) —C($R^{16a}$)—,
- (2) —C$R^{17}R^{18}$—,
- (3) —C(=O)—, and
- (4) —N($R^b$)—, then L must be selected from:
- (1) —C(=S)—,
- (2) —SO$_2$—,
- (3) —SO—, and
- (4) —C$R^gR^h$;

$R^{17}$ and $R^{18}$ are each independently selected from:
- (1) hydrogen,
- (2) halo,
- (3) —O$R^a$,
- (4) —C$_{1-6}$alkyl, which is unsubstituted or substituted with 1-4 substituents each independently selected from:
  - (a) halo,
  - (b) —O$R^a$,
  - (c) —CN,
  - (d) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
    - (i) —O$R^a$,
    - (ii) halo,
    - (iii) —CN,
    - (iv) —C$_{1-6}$alkyl which is unsubstituted or substituted with 1-6 halo,
- (5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
  - (a) halo,
  - (b) —CN,
  - (c) —O$R^a$,
  - (d) nitro,
  - (e) —C$_{1-6}$alkyl which is unsubstituted or substituted with 1-6 halo, or $R^{17}$ and $R^{18}$ and the atom to which they are attached join to form a 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
- (a) halo,
- (b) —O$R^a$,
- (c) —C$_{1-6}$alkyl, which is unsubstituted or substituted with 1-6 halo, and
- (d) phenyl;

$R^{16a}$ and $R^{16b}$ are each independently selected from:
- (1) hydrogen,
- (2) —C$_{1-4}$alkyl, which is unsubstituted or substituted with 1-5 substituents each independently selected from:
  - (a) halo,
  - (b) —O$R^a$,
  - (c) —C$_{3-6}$cycloalkyl,
  - (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is unsubstituted or substituted with 1-3 substituents each independently selected from:
    - (i) halo,
    - (ii) —O$R^a$,
    - (iii) —CN, and
    - (iv) C$_{1-6}$alkyl, which is unsubstituted or substituted with 1-6 halo,
- (3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is unsubstituted or substituted with 1-3 substituents each independently selected from:
  - (a) halo,
  - (b) —O$R^a$,
  - (c) —C$_{3-6}$cycloalkyl,
  - (d) —C$_{1-4}$alkyl which is unsubstituted or substituted with 1-6 halo, and
  - (e) phenyl, which is unsubstituted or substituted with 1-5 substituents each independently selected from:
    - (i) halo,
    - (ii) —C$_{1-6}$alkyl, which is unsubstituted or substituted with 1-6 halo, and
    - (iii) —O$R^a$,
- (4) halo,
- (5) —O$R^a$,
- (6) —CN,
- (7) —CO$_2R^a$,
- (8) —N$R^bR^c$,
- (9) —C(=O)N$R^bR^c$, and
- (10) —C$_{3-6}$cycloalkyl which is unsubstituted or substituted with 1-6 halo, or $R^{16a}$ and $R^{16b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:

(a) —$C_{1-6}$alkyl, which is unsubstituted or substituted with 1-3 substituents each independently selected from:
   (i) halo,
   (ii) —$OR^a$,
   (iii) —$C_{3-6}$cycloalkyl,
   (iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
      (I) —$OR^a$,
      (II) halo,
      (III) —CN, and
      (IV) —$C_{1-6}$alkyl which is unsubstituted or substituted with 1-6 halo,
   (v) —$CO_2R^a$,
   (vi) —$NR^bR^c$,
   (vii) —$S(O)_vR^d$,
   (viii) —$C(=O)NR^bR^c$,
   (ix) —$N(R^b)CO_2R^a$, and
   (x) —$N(R^b)SO_2R^d$,
(b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-5 substituents each independently selected from:
   (i) halo,
   (ii) —$OR^a$,
   (iii) —CN, and
   (iv) —$C_{1-6}$alkyl which is unsubstituted or substituted with 1-6 halo,
(c) halo,
(d) —$S(O)_vR^d$,
(e) —$OR^a$,
(f) —CN,
(g) —$C(=O)R^a$,
(h) —$NR^bR^c$,
(i) —$C(=O)NR^bR^c$,
(j) —$CO_2R^a$,
(k) —$(NR^b)CO_2R^a$,
(l) —O—(C=O)—$NR^bR^c$,
(m) —$(NR^b)$—(C=O)—$NR^bR^c$,
(n) oxido,
(o) oxo, and
(p) —$(NR^b)SO_2R^d$;

$R^a$ is independently selected from:
(1) hydrogen,
(2) $C_{1-6}$alkyl, which is unsubstituted or substituted with 1-7 substituents each independently selected from:
   (a) halo,
   (b) —O—$C_{1-6}$alkyl, which is unsubstituted or substituted with 1-6 halo,
   (c) hydroxyl,
   (d) —CN, and
   (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —O—$C_{1-6}$alkyl, which is unsubstituted or substituted with 1-6 halo,
      (iii) —CN,
      (iv) nitro,
      (v) hydroxyl, and
      (vi) —$C_{1-6}$alkyl, which is unsubstituted or substituted with 1-6 halo,
(3) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
   (a) halo,
   (b) —CN,
   (c) —O—$C_{1-6}$alkyl, which is unsubstituted or substituted with 1-6 halo,
   (d) nitro,
   (e) hydroxyl, and
   (f) —$C_{1-6}$alkyl, which is unsubstituted or substituted with 1-6 halo, and
(4) —$C_{3-6}$cycloalkyl, which is unsubstituted or substituted with 1-6 halo;

$R^b$ and $R^c$ are independently selected from:
(1) hydrogen,
(2) $C_{1-6}$alkyl, which is unsubstituted or substituted with 1-7 substituents each independently selected from:
   (a) halo,
   (b) —$OR^a$,
   (c) —CN,
   (d) —$CO_2R^a$,
   (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —$OR^a$,
      (iii) —$C_{1-6}$alkyl, which is unsubstituted or substituted with 1-6 halo, and
      (iv) nitro,
(3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
   (a) halo,
   (b) —$OR^a$,
   (c) —$C_{1-6}$alkyl, which is unsubstituted or substituted with 1-6 halo,
   (d) —$C_{3-6}$cycloalkyl, which is unsubstituted or substituted with 1-6 halo,
   (e) —CN, and
   (f) —$CO_2R^a$,
(4) —$C_{3-6}$cycloalkyl, which is unsubstituted or substituted with 1-6 halo,
or $R^b$ and $R^c$ and the nitrogen to which they are attached join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from:
(a) halo,
(b) —OR$^a$, and
(c) —C$_{1-6}$alkyl, which is unsubstituted or substituted with 1-6 halo, and
(d) phenyl;

R$^d$ is independently selected from:
(1) C$_{1-6}$alkyl, which is unsubstituted or substituted with 1-4 substituents each independently selected from:
(a) halo,
(b) —OR$^a$,
(c) —CO$_2$R$^a$,
(d) —CN, and
(e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
(i) halo,
(ii) —OR$^a$,
(iii) —C$_{1-6}$alkyl, which is unsubstituted or substituted with 1-6 halo, and
(iv) nitro,
(2) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
(a) halo,
(b) —OR$^a$,
(c) —C$_{1-6}$alkyl, which is unsubstituted or substituted with 1-6 halo,
(d) —C$_{3-6}$cycloalkyl, which is unsubstituted or substituted with 1-6 halo
(e) —CN, and
(f) —CO$_2$R$^a$, and
(3) —C$_{3-6}$cycloalkyl, which is unsubstituted or substituted with 1-6 halo;

R$^e$ and R$^f$ are independently selected from:
(1) hydrogen,
(2) —C$_{1-4}$alkyl, which is unsubstituted or substituted with 1-6 halo,
(3) phenyl, and
(4) benzyl;
or R$^e$ and R$^f$ and the atom to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
(a) halo,
(b) —OR$^a$,
(c) —C$_{1-6}$alkyl, which is unsubstituted or substituted with 1-6 halo, and
(d) phenyl;

R$^g$ and R$^h$ are independently selected from:
(1) hydrogen,
(2) halo,
(3) —C$_{1-4}$alkyl, which is unsubstituted or substituted with 1-6 halo,
(4) phenyl, and
(5) benzyl;
or where R$^g$ and R$^h$ and the atom to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
(a) halo,
(b) —OR$^a$,
(c) —C$_{1-6}$alkyl, which is unsubstituted or substituted with 1-6 halo, and
(d) phenyl;

v is 0, 1, or 2;
k is 0, 1, or 2;
and pharmaceutically acceptable salts thereof and individual enantiomers and diastereomers thereof.

In particular embodiments, A$^1$ is selected from:
(1) —O—,
(2) —S(O)$_v$— (for example, where v is 0),
(3) —CR$^6$R$^7$— or
(4) —N(R$^8$)—.

In particular embodiments, A$^1$ is —NR$^8$, wherein R$^8$ is preferably H or —C$_{1-3}$alkyl (preferably methyl).

In particular embodiments, A$^2$ is selected from:
(1) —CR$^6$R$^7$—, or
(2) —CR$^{10}$R$^{11}$—. Typically, when A$^2$ is —CR$^6$R$^7$—, and A$^4$ is a bond, then R$^6$ and R$^7$ are each hydrogen, or one of R$^6$ and R$^7$ is hydrogen, and the other is linked together with an R$^6$ or R$^7$ from the A$^3$ group to form a ring selected from cyclopropyl, cyclobutyl, cyclopentyl, cyclohexyl, cycloheptyl, cyclooctyl, cyclononyl, cyclobutenyl, cyclopentenyl, cyclohexenyl, cycloheptenyl, cyclooetenyl, dioxolanyl, dioxanyl, indanyl, aziridinyl, azetidinyl, pyrrolidinyl, piperidinyl, piperazinyl, morpholinyl, tetrahydrofuranyl, tetrahydropyranyl, tetrahydrothiapyranyl, oxetanyl, thietanyl and tetrahydrothienyl, wherein the sulfur is optionally oxidized to the sulfone or sulfoxide, which ring is optionally substituted as described above.

In particular embodiments, A$^3$ is selected from:
(1) —CR$^6$R$^7$—, or
(2) —CR$^{10}$R$^{11}$—. Typically, when A$^3$ is —CR$^6$R$^7$—, and A$^4$ is a bond, then R$^6$ and R$^7$ are each hydrogen, or one of R$^6$ and R$^7$ is hydrogen, and the other is linked together with an R$^6$ or R$^7$ from the A$^2$ group to form a ring selected from cyclopropyl, cyclobutyl, cyclopentyl, cyclohexyl, cycloheptyl, cyclooctyl, cyclononyl, cyclobutenyl, cyclopentenyl, cyclohexenyl, cycloheptenyl, cyclooctenyl, dioxolanyl, dioxanyl, indanyl, aziridinyl, azetidinyl, pyrrolidinyl, piperidinyl, piperazinyl, morpholinyl, tetrahydrofuranyl, tetrahydropyranyl, tetrahydrothiapyranyl, oxetanyl, thietanyl and tetrahydrothienyl, wherein the sulfur is optionally oxidized to the sulfone or sulfoxide, which ring is optionally substituted as described above.

When A$^3$ is —CR$^{10}$R$^{11}$—, then typically R$^{10}$ is hydrogen, and R$^{11}$ is optionally substituted phenyl.

In particular embodiments, A$^4$ is selected from:
(1) —CR$^6$R$^7$—,
(2) —CR$^{10}$R$^{11}$—, or
(3) a bond.

In particular embodiments of the invention, A$^4$ is a bond.

In particular embodiments, A$^5$ and A$^7$ are each independently selected from:
(1) —CH$_2$—, or
(2) a bond.

In particular embodiments, A$^5$ and A$^7$ are each a bond.

In particular embodiments, $A^6$ and $A^8$ are independently selected from:
(1) —O—,
(2) —CR$^{15a}$H, or
(3) —CH$_2$—. Typically, when one of $A^6$ and $A^8$ are —CR$^{15a}$H, then R$^{15a}$ is halogen or —C$_{1-6}$alkyl, which is optionally substituted with halogen.

In particular embodiments, E$^a$, E$^b$ and E$^c$ are each independently selected from:
(1) —C(R$^5$)=, or
(2) —N=. Typically, when any of E$^a$, E$^b$ or E$^c$ are —C(R$^5$)=, then R$^5$ is hydrogen. In particular embodiments, E$^b$ is nitrogen, and E$^a$ and E$^c$ are each CH.

In particular embodiments, L is selected from:
(1) —C(=O)—, or
(2) —C(=S)—.

In particular embodiments, Q is —(C=O)—.

In particular embodiments, R$^4$ is selected from:
(1) hydrogen, or
(2) —C$_{1-6}$alkyl, which is unsubstituted or substituted with 1-5 substituents each independently selected from:
(a) halo,
(b) —C$_{3-6}$cycloalkyl,
(c) —CF$_3$, and
(d) —O—R$^a$.

In particular embodiments, R$^{PG}$ is selected from:
(1) hydrogen, or
(2) —C$_{1-6}$alkyl which is unsubstituted or substituted with 1-5 halo, In particular embodiments, J is selected from:
(1) =C(R$^{16a}$)—,
(2) —CR$^{17}$R$^{18}$—, or
(3) —N(R$^b$)—;

In particular embodiments, Y is selected from:
(1) =C(R$^{16h}$)—,
(2) —CR$^{17}$R$^{18}$—, or
(3) —C(=O)—.

In particular embodiments, J is =C(R$^{16a}$)—, and Y is =C(R$^{16b}$)—, and R$^{16a}$ and R$^{16b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is optionally substituted as described above.

In particular embodiments, W is selected from:
(1) a bond, or
(2) —O—.

In particular embodiments, Z is selected from:
(1) a bond, or
(2) —O—,
wherein when W and Z are both selected to be a bond and J is selected from:
(1) =C(R$^{16a}$)—,
(2) —CR$^{17}$R$^{18}$—, or
(3) —C(=O)—,
then L must be selected from:
(1) —C(=S)—,
(2) —CR$^g$R$^h$.

In some embodiments, R$^e$ and R$^f$ are independently selected from:
(1) hydrogen,
(2) —C$_{1-4}$alkyl, which is unsubstituted or substituted with 1-6 halo, or R$^e$ and R$^f$ and the atom to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
(a) halo,
(b) —OR$^a$,
(c) —C$_{1-6}$alkyl, which is unsubstituted or substituted with 1-6 halo, and
(d) phenyl.

In some embodiments, R$^e$ and R$^f$ are each hydrogen, or R$^e$ and R$^f$ and the atom to which they are attached are joined to form cycloalkyl (typically, cyclopropyl).

In particular embodiments, R$^6$ and R$^7$ are each hydrogen or —C$_{1-4}$alkyl (typically, methyl).

The present invention is further directed to the exemplary compounds 1 and 2 of formula (I):
1-(2-Oxo-5-phenylpiperazin-1-yl)-N-(3'-thioxo-3',4',5,7-tetrahydrospiro[cyclopenta[b]pyridine-6,2'-pyrido[3,2-b][1,4]oxazin]-3-yl)cyclopropanecarboxamide;
2-(3,4-dimethyl-2-oxo-6-phenylpiperazin-1-yl)-N-(2'-oxo-1,1',2',3-tetrahydrospiro[indene-2,4'-pyrido[2,3-d][1,3]oxazin]-5-yl)acetamide;
and pharmaceutically acceptable salts thereof.

The invention is also directed to medicaments or pharmaceutical compositions for treating diseases or disorders in which CGRP is involved, such as migraine, which comprise a compound of any of formulas (I) to (III), or a pharmaceutically acceptable salt thereof, and a pharmaceutically acceptable carrier.

The invention is also directed to the use of a compound of any of formulas (I) to (III) for treating diseases or disorders in which CGRP is involved, such as migraine.

The invention is further directed to a method for the manufacture of a medicament or a composition for treating diseases or disorders in which CGRP is involved, such as migraine, comprising combining a compound of any of formulas (I) to (III) with one or more pharmaceutically acceptable carriers.

It is to be understood that where one or more of the above recited structures or substructures recite multiple substituents having the same designation each such variable may be the same or different from each similarly designated variable. For example, R$^a$ is recited multiple times in formula I, and each R$^a$ in formula I may independently be any of the substructures defined under R$^a$. The invention is not limited to structures and substructures wherein each R$^a$ must be the same for a given structure. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The present invention includes compounds of formula I wherein on or more hydrogen atoms are replaced by deuterium.

Tautomers of compounds defined in any of formulas (I) to (III) are also included within the scope of the present invention. For example, compounds including carbonyl —CH$_2$C (O)— groups (keto forms) may undergo tautomerism to form hydroxyl —CH=C(OH)— groups (enol forms). Both keto and enol forms are included within the scope of the present invention.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, even where substituents are disclosed which may form a ring structure (for instance $R^6$ may form a ring with $R^7$), not all combinations of substituents are susceptible to ring formation. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear and branched structures having no carbon-to-carbon double or triple bonds. Thus $C_{1-6}$alkyl is defined to identify the group as having 1, 2, 3, 4, 5 or 6 carbons in a linear or branched arrangement, such that $C_{1-6}$alkyl specifically includes, but is not limited to, methyl, ethyl, n-propyl, iso-propyl, n-butyl, iso-butyl, tert-butyl, pentyl and hexyl. $C_0$ or $C_0$alkyl is defined to identify the presence of a direct covalent bond.

"Cycloalkyl" is an alkyl, part or all of which forms a ring of three or more atoms.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "$(F)_p C_{1-3}$ alkyl" this means that when there is one carbon, there are up to 2(1)+1=3 fluorines. When there are two carbons, there are up to 2(2)+1=5 fluorines, and when there are three carbons there are up to 2(3)+1=7 fluorines.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of any of Formulas (I) to (III) or the other drugs may have utility, where the combination of the drugs together are safer or more effective than either drug alone. Such other drug(s) may be administered, by a route and in an amount commonly used therefor, contemporaneously or sequentially with a compounds of any of Formulas (I) to (III). When a compound of any of Formulas (I) to (III) is used contemporaneously with one or more other drugs, a pharmaceutical composition in unit dosage form containing such other drugs and the compound of any of Formulas (I) to (III) is preferred. However, the combination therapy may also include therapies in which the compound of any of Formulas (I) to (III) and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of any of Formulas (I) to (III).

For example, the present compounds may be used in conjunction with an anti-migraine agent, such as ergotamine and dihydroergotamine, or other serotonin agonists, especially a 5-HT$_{1B/1D}$ agonist, for example sumatriptan, naratriptan, zolmitriptan, eletriptan, almotriptan, frovatriptan, donitriptan, and rizatriptan, a 5-HT$_{1D}$ agonist such as PNU-142633 and a 5-HT$_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5HT$_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, caraberzat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, poly-vinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligram to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Reaction Schemes

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Simple modifications of these routes, including different protecting group strategies, application of well-precedented methodology, and the use of starting materials and reagents other than those described in the foregoing schemes, may be used to provide other intermediates and claimed compounds.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reactions schemes may be varied to facilitate the reaction or to avoid unwanted reaction products.

The following examples are provided so that the invention might be more fully understood. These examples are illustrative only and should not be construed as limiting the invention in any way.

SCHEME 1

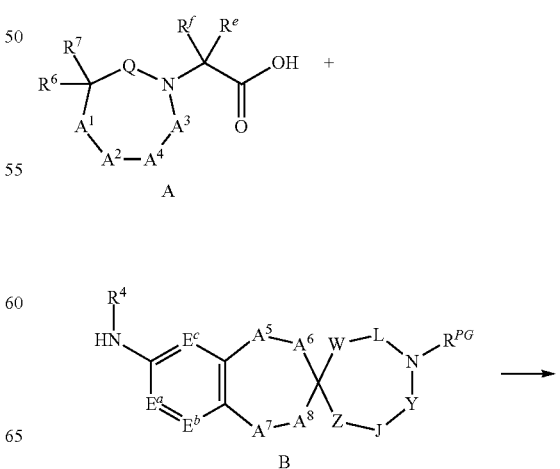

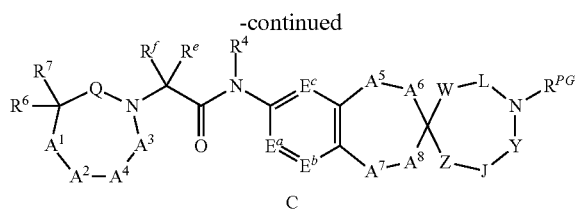

C

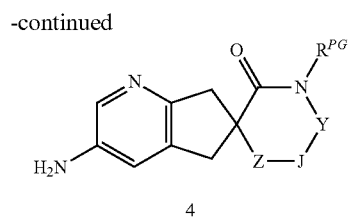

4

Scheme 1 illustrates a general strategy for the synthesis of the compounds of the present invention via coupling of carboxylic acid A with amine B to give amide C. Standard coupling conditions, such as EDC and HOBT with DIEA as base and DMF as solvent, may be successfully employed in this reaction. Other standard coupling conditions may be employed in the synthesis of such amides, including use of an alternative coupling reagent such as BOP, HATU or PyCLU, or activation of the carboxylic acid as an acid anhydride or acid chloride. In some cases, various protecting group strategies familiar to one skilled in the art of organic synthesis may be employed to allow preparation of a particular compound of the present invention.

Most of the acids A used to make the compounds of the present invention are readily available. They may be obtained from commercial sources or synthesized by methodology familiar to those skilled in the art and as described in the chemical literature. Many of the acids A of interest are also described in Wood et al US 2007/0265225.

The amines B used to make the compounds of the present invention can be prepared readily according to the following Schemes and specific examples, or modifications thereof, using readily available starting materials, reagents and conventional synthesis procedures.

As shown in Scheme 2, intermediate 1 (such as commercially available 2H-pyrido[3,2-b][1,4]oxazin-3(4H)-one) may undergo spirocyclization with the known 1,4-dibromobutanone (Meijere et al. (2001) *Eur. J. Org. Chem.* 20, 3789) to afford spiroketone 2. Condensation of 2 with 1-methyl-3,5-dinitropyridinone (Tohda et al. (1990) *Bull. Chem. Soc. Japan* 63, 2820) in refluxing methanolic ammonia provides nitropyridine 3 which undergoes iron-mediated reduction to aminopyridine 4. Additionally, oxazinone 1 may undergo spirocyclization with other dihalides or bis-sulfonates as an alternate approach to the synthesis of intermediates like 3 for use in the preparation of compounds described in the present invention, using methods which are known to those skilled in the art and described in the chemical literature.

SCHEME 3

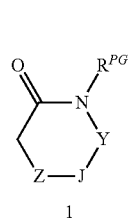

5

SCHEME 2

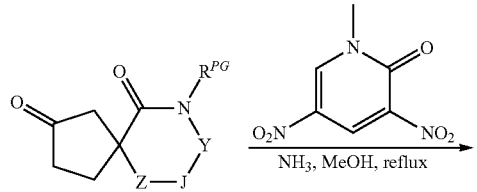

1

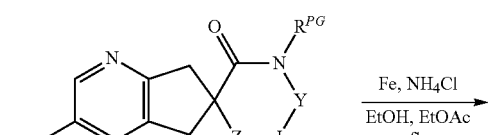

2

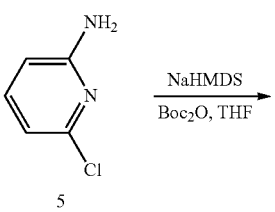

6

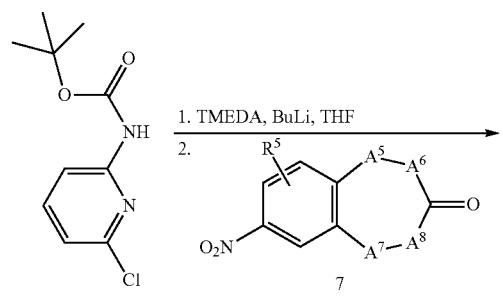

7

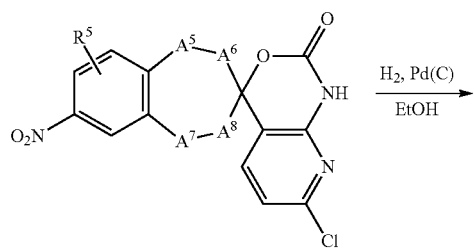

8

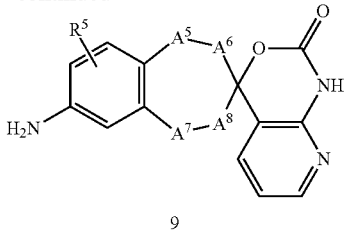

9

As depicted in Scheme 3, 2-amino-6-chloropyridine 5 is converted to its Boc derivative 6 as described in Williams US2006/028835. Ortho-metallation of 6 under conditions described in Davies et al (2004) *Tetrahedron Lett.* 45, 1721 followed by addition of the resultant anion to ketone 7 and in situ cyclization affords spiropyridooxazinone 8. One-pot reduction and dechlorination affords amine 9, which may be used in the preparation of compounds described in the present invention. Other ketones 7, such as but not limited to 5-haloindanones, may be subjected to a similar addition-cyclization sequence followed by further derivatization to amines 9, utilizing synthesis procedures described in the chemical literature and known to those skilled in the art. Various protecting group strategies and other modifications to the steps in the scheme may be employed, and such modifications would be known to those skilled in the art.

The methodology shown in these schemes is not meant to limit the scope of the invention, but only to give representative examples and intermediates. Related intermediates and examples bearing a variety of substituents may be prepared by using appropriately substituted starting materials or by derivatization of any intermediates and/or final products as desired by methods known in the art. Resolutions may be affected by other methodologies, such as fractional crystallization or diastereomeric salts, and it may be carried out on other synthetic intermediates or on the final products. Alternatively, an asymmetric synthesis of a key intermediate could be used to provide an enantiomerically enriched final product.

In some cases the final product may be further modified, for example, by manipulation of substituents. These manipulations may include, but are not limited to, reduction, oxidation, alkylation, acylation, and hydrolysis reactions which are commonly known to those skilled in the art. Moreover, in some cases the order of carrying out the foregoing reaction schemes may be varied to facilitate the reaction or to avoid unwanted reaction products.

INTERMEDIATES AND EXAMPLES

The following examples are provided so that the invention might be more fully understood. These examples are illustrative only and should not be construed as limiting the invention in any way.

Intermediate 1

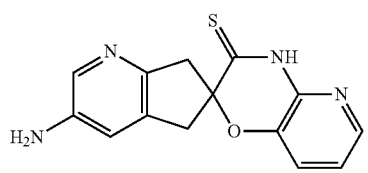 [SMILES: Nc1cnc2c(c1)CC1(C2)Oc2cccnc2NC1=S]

3-Amino-5,7-dihydrospiro[cyclopenta[b]pyridine-6, 2'-pyrido[3,2-b][1,4]oxazine]-3'(4'H)-thione Step A. 4-{[2-(Trimethylsilyl)ethoxy]methyl}-2H-pyrido[3,2-b][1,4]oxazin-3(4H)-one Sodium hydride (60% dispersion in mineral oil; 0.48 g, 12 mmol) is added in portions to a solution of 2H-pyrido[3,2-b][1,4]oxazin-3(4H)-one (1.50 g, 10 mmol) in DMF (20 mL) at 0° C. and the mixture is stirred for 1 h. 2-(Trimethylsilyl)ethoxymethylchloride (2.1 mL, 12 mmol) is added slowly dropwise and the mixture is then stirred at rt for 1 h. The reaction is quenched by pouring into ice-water and the mixture is then extracted with $CH_2Cl_2$ (×3). The combined organic extracts are washed with brine, dried ($MgSO_4$), filtered and concentrated in vacuo. The crude product is purified by silica gel chromatography (gradient elution with hexanes-EtOAc) to afford the title compound.

Step B. 4'-{[2-(Trimethylsilyl)ethoxy]methyl}-3H-spiro[cyclopentane-1,2'-pyrido[3,2-b][1,4]oxazine]-3,3'(4'H)-dione A solution of 4-{[2-(trimethylsilyl)ethoxy]methyl}-2H-pyrido[3,2-b][1,4]oxazin-3(4H)-one from Step A (1.40 g, 5.0 mmol) and cesium carbonate (3.58 g, 11 mmol) in DMF (25 mL) is treated dropwise with a solution of 1,4-dibromobutan-2-one (0.84 g, 6.5 mmol) [Meijere et al. (2001) *Eur. J. Org. Chem* 20, 3789] in DMF (25 mL). The mixture is stirred at rt for 18 h and is then partitioned between $Et_2O$ and water. The layers are separated and the aqueous layer further extracted with $Et_2O$ (×2). The combined organic layers are dried ($Na_2SO_4$), filtered and concentrated in vacuo. The crude product is purified by silica gel chromatography (gradient elution with hexanes-EtOAc) to afford the title compound.

Step C. 3-Nitro-4'-{[2-(trimethylsilyl)ethoxy]methyl}-5,7-dihydrospiro[cyclopenta[b]pyridine-6,2'-pyrido[3,2-b][1,4]oxazin]-3'(4'H)-one A mixture of 4'-{[2-(trimethylsilyl)ethoxy]methyl}-3H-spiro[cyclopentane-1,2'-pyrido[3,2-b][1,4]oxazine]-3,3'(4'H)-dione from Step B (1.05 g, 3.0 mmol) and 1-methyl-3,5-dinitropyridin-2(1H)-one (0.75 g, 3.8 mmol) [Tohda et al. (1990) *Bull. Chem. Soc. Japan* 63, 2820] in 2 M ammonia in MeOH (15 mL) is refluxed for 18 h. The mixture is concentrated in vacuo and the residue is purified by silica gel chromatography (gradient elution with hexanes-EtOAc) to afford the title compound.

Step D. 3-Nitro-5,7-dihydrospiro[cyclopenta[b]pyridine-6,2'-pyrido3,2-b][1,4oxazin]-3'(4'H)-one A solution of 3-nitro-4'-{[2-(trimethylsilyl)ethoxy]methyl}-5,7-dihydrospiro[cyclopenta[b]pyridine-6,2'-pyrido[3,2-b][1,4]oxazin]-3'(4H)-one from Step C (430 mg, 1.0 mmol) in $CH_2Cl_2$ (12 mL) and TFA (4 mL) is stirred at rt for 30 min. The volatiles are removed in vacuo and the residue is taken up in MeOH (10 mL) and treated with ethylenediamine (0.065 mL, 1.0 mmol). The mixture is adjusted to pH 10 by addition of 10 N aqueous sodium hydroxide and the mixture is then stirred at rt for 1 h. The pH is readjusted to 6 by addition of acetic acid and the mixture is then extracted with $CH_2Cl_2$ (×3). The combined organic extracts are dried ($Na_2SO_4$), filtered and concentrated in vacuo. The residue is purified by silica gel chromatography (gradient elution with 0-10% MeOH in $CH_2Cl_2$) to afford the title compound.

Step E. 3-Nitro-5,7-dihydrospiro[cyclopenta[b]pyridine-6,2'-pyrido[3,2-b][1,4]oxazine]-3'(4'H)-thione A solution of 3-nitro-5,7-dihydrospiro[cyclopenta[b]pyridine-6,2'-pyrido[3,2-b][1,4]oxazin]-3'(4'H)-one from Step D (450 mg, 1.5 mmol) in toluene (3 mL) is treated with Lawesson's reagent (650 mg, 1.6 mmol) and the mixture heated at reflux for several hours. The solvent is removed in vacuo and the residue is purified by silica gel chromatography (gradient elution with 0-10% MeOH in $CH_2Cl_2$) to afford the title compound.

Step F. 3-Amino-5,7-dihydrospiro[cyclopenta[b]pyridine-6,2'-pyrido[3,2-b][1,4]oxazine]-3'(4'H)-thione A solution of 3-nitro-5,7-dihydrospiro[cyclopenta[b]pyridine-6,2'-pyrido[3,2-b][1,4]oxazine]-3'(4'H)-thione from Step E (628 mg, 2.0 mmol) in EtOH (16 mL) and EtOAc (8 mL) is treated successively with water (8 mL), iron powder (558 mg, 10 mmol) and ammonium chloride (53.5 mg, 1.0 mmol). The mixture is heated at reflux for 3 h and is then cooled to rt and filtered, washing the solids with additional EtOH. The filtrate is concentrated in vacuo and the residue is partitioned between EtOAc and saturated aqueous $NaHCO_3$. The layers are separated and the organic layer is washed with brine, dried ($Na_2SO_4$), filtered and concentrated in vacua, The residue is purified by silica gel chromatography (gradient elution with 0-10% MeOH in $CH_2Cl_2$) to afford the title compound.

Intermediate 2

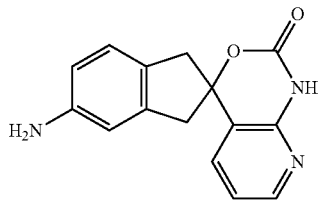 [SMILES: Nc1ccc2c(c1)CC1(C2)OC(=O)Nc2ncccc21]

5-Amino-1,3-dihydrospiro[indene-2,4'-pyrido[2,3-d][1,3]oxazin]-2'(1'H)-one

Step A. 7'-Chloro-5-nitro-1,3-dihydrospiro[indene-2,4'-pyrido[2,3-d][1,3]oxazin]-2'(1'H)-one A solution of N,N,N',N'-tetramethylethylenediamine (3.3 mL, 22 mmol) in THF (8 mL) is cooled to −20° C. and treated with n-butyllithium (2.5 M in hexanes, 8.8 mL, 22 mmol) over 10 min. After stirring for 30 min, the mixture is cooled to −78° C. and treated with a solution of tert-butyl(6-chloropyridin-2-yl)carbamate (2.29 g, 10 mmol) [Williams US2006/028835] in THF (6 mL) over 15 min. After 1 h, the mixture is warmed to −50° C. and treated with a solution of 5-nitro-1,3-dihydro-2H-inden-2-one (2.66 g, 15 mmol) in THF (8 mL) over 10 min. The mixture is then allowed to warm to rt and stirred for 24 h. The reaction is quenched by addition of saturated aqueous $NaHCO_3$ and the mixture is then extracted with EtOAc (×3). The combined organic extracts are washed successively with water and brine, dried (anhydrous $MgSO_4$), filtered and concentrated in vacuo. The residue is purified by silica gel chromatography (gradient elution with hexanes-EtOAc) to afford the title compound.

Step B. 5-Amino-1,3-dihydrospiro[indene-2,4'-pyrido[2,3-d][1,3]oxazin]-2'(1'H)-one A mixture of 7'-chloro-5-nitro-1,3-dihydrospiro[indene-2,4'-pyrido[2,3-d][1,3]oxazin]-2'(1H)-one from Step A (1.0 g, 3.0 mmol) and 10% palladium on carbon (200 mg) in EtOH (300 mL) is stirred under hydrogen atmosphere for 24 h. The mixture is then filtered through Celite and the filtrate concentrated to give the title compound.

Example 1

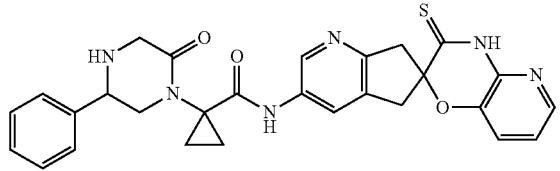 [SMILES: O=C1CNC(c2ccccc2)CN1C1(C(=O)Nc2cnc3c(c2)CC2(C3)Oc3cccnc3NC2=S)CC1]

1-(2-Oxo-5-phenylpiperazin-1-yl)-N-(3'-thioxo-3',4',5,7-tetrahydrospiro[cyclopenta[b]pyridine-6,2'-pyrido[3,2-b][1,4]oxazin]-3-yl)cyclopropanecarboxamide A mixture of 1-(2-oxo-5-phenylpiperazin-1-yl)cyclopropanecarboxylic acid hydrochloride (57 mg, 0.22 mmol) [Wood et al. US 2007/0265225], 3-amino-5,7-dihydrospiro[cyclopenta[b]pyridine-6,2'-pyrido[3,2-b][1,4]oxazine]-3'(4'H)-thione (Intermediate 1, 57 mg, 0.20 mmol) and HATU (84 mg, 0.22 mmol) in DMF (2 mL) is treated with N-methylmorpholine (0.096 mL, 0.88 mmol). The mixture is stirred at rt for 18 h and is then purified directly by HPLC using a reversed phase C18 column and eluting with a gradient of $H_2O:CH_3CN:CF_3CO_2H$—90:10:0.1 to 5:95:0.1. The pure, product-containing fractions are combined and lyophilized to afford the title compound.

Example 2

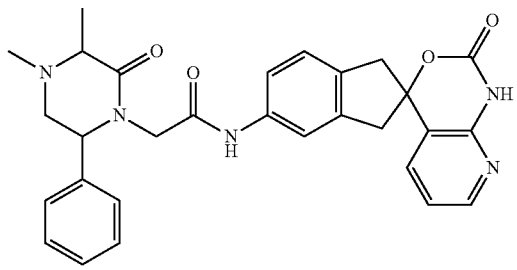 [SMILES: CC1C(=O)N(CC(=O)Nc2ccc3c(c2)CC2(C3)OC(=O)Nc3ncccc32)C(c2ccccc2)CN1C]

2-(3,4-Dimethyl-2-oxo-6-phenylpiperazin-1-yl)-N-(2'-oxo-1,1',2',3-tetrahydrospiro[indene-2,4'-pyrido[2,3-d][1,3]oxazin]-5-yl)acetamide A mixture of lithium(3,4-dimethyl-2-oxo-6-phenylpiperazin-1-yl)acetate (30 mg, 0.11 mmol) [Wood et al. US 2007/

0265225], 5-amino-1,3-dihydrospiro[indene-2,4'-pyrido[2,3-d][1,3]oxazin]-2'(1'H)-one (Intermediate 2, 27 mg, 0.10 mmol) and HATU (42 mg, 0.11 mmol) in DMF (1 mL) is treated with N-methylmorpholine (0.036 mL, 0.33 mmol). The mixture is stirred at rt for 18 h and is then purified directly by HPLC using a reversed phase C18 column and eluting with a gradient of $H_2O:CH_3CN:CF_3CO_2H$—90:10:0.1 to 5:95:0.1. The pure, product-containing fractions are combined and lyophilized to afford the title compound.

The utility of the compounds in accordance with the present invention as antagonists of CGRP receptor activity may be demonstrated by methodology known in the art. Inhibition of the binding of $^{125}I$-CGRP to receptors and functional antagonism of CGRP receptors may be determined as follows:

NATIVE RECEPTOR BINDING ASSAY: The binding of $^{125}I$-CGRP to receptors in SK-N-MC cell membranes according to this procedure may be carried out essentially as described (Edvinsson et al. (2001) *Eur. J. Pharmacol.* 415, 39-44). Briefly, according to this procedure, membranes (25 µg) are incubated in 1 mL of binding buffer [10 mM HEPES, pH 7.4, 5 mM $MgCl_2$ and 0.2% bovine serum albumin (BSA)] containing 10 pM $^{125}I$-CGRP and antagonist. After incubation at room temperature for 3 h, the assay is terminated by filtration through GFB glass fibre filter plates (PerkinElmer) that had been blocked with 0.5% polyethyleneimine for 3 h. The filters are washed three times with ice-cold assay buffer (10 mM HEPES, pH 7.4 and 5 mM $MgCl_2$), then the plates are air dried. Scintillation fluid (50 µL) is added and the radioactivity is counted on a Topcount (Packard Instrument). Data analysis is carried out by using Prism and the $K_i$ is determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) is subcloned into the expression vector pIREShyg2 (BD Biosciences Clontech) as a 5'NheI and 3' PmeI fragment. Human RAMP1 (Genbank accession number AJ001014) is subcloned into the expression vector pIRESpuro2 (BD Biosciences Clontech) as a 5'NheI and 3'NotI fragment. HEK 293 cells (human embryonic kidney cells; ATCC #CRL-1573) are cultured in DMEM with 4.5 g/L glucose, 1 mM sodium pyruvate and 2 mM glutamine supplemented with 10% fetal bovine serum (FBS), 100 units/mL penicillin and 100 µg/mL streptomycin, and maintained at 37° C. and 95% humidity. Cells are subcultured by treatment with 0.25% trypsin with 0.1% EDTA in HBSS. Stable cell line generation is accomplished by co-transfecting 10 µg of DNA with 30 µg Lipofectamine 2000 (Invitrogen) in 75 cm² flasks. CL receptor and RAMP1 expression constructs are co-transfected in equal amounts. Twenty-four hours after transfection the cells are diluted and selective medium (growth medium+300 µg/mL hygromyein and 1 µg/mL puromycin) is added the following day. A clonal cell line is generated by single cell deposition utilizing a FACS Vantage SE (Becton Dickinson). Growth medium is adjusted to 150 µg/mL hygromycin and 0.5 µg/mL puromycin for cell propagation.

RECOMBINANT RECEPTOR BINDING ASSAY: Cells expressing recombinant human CL receptor/RAMP1 may be washed with PBS and harvested in harvest buffer containing 50 mM HEPES, 1 mM EDTA and Complete protease inhibitors (Roche). The cell suspension is disrupted with a laboratory homogenizer and centrifuged at 48,000 g to isolate membranes. The pellets are resuspended in harvest buffer plus 250 mM sucrose and stored at −70° C. For binding assays, 20 µg of membranes are incubated in 1 ml binding buffer (10 mM HEPES, pH 7.4, 5 mM $MgCl_2$, and 0.2% BSA) for 3 hours at room temperature containing 10 pM $^{125}I$-hCGRP (GE Healthcare) and antagonist. The assay is terminated by filtration through 96-well GFB glass fiber filter plates (PerkinElmer) that had been blocked with 0.05% polyethyleneimine. The filters are washed 3 times with ice-cold assay buffer (10 mM HEPES, pH 7.4 and 5 mM $MgCl_2$). Scintillation fluid is added and the plates are counted on a Topcount (Packard). Non-specific binding is determined and the data analysis is carried out with the apparent dissociation constant $(K_i)$ determined by using a non-linear least squares fitting the bound CPM data to the equation below:

$$Y_{obsd} = \frac{Y_{min} + (Y_{max} - Y_{min})(100 - \% \, I_{max}/100)}{1 + ([Drug]/K_i(1 + [Radiolabel]/K_d)^{nH})} + \frac{(Y_{max} - Y_{min})(\% \, I_{max} - \% \, I_{min}/100)}{}$$

Where Y is observed CPM bound, $Y_{max}$ is total bound counts, $Y_{min}$ is non specific bound counts, $(Y_{max}-Y_{min})$ is specific bound counts, % $I_{max}$ is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells may be plated in complete growth medium at 85,000 cells/well in 96-well poly-D-lysine coated plates (Corning) and cultured for ~19 h before assay. According to this procedure, cells are washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine is added to the cells at a concentration of 300 µM and incubated for 30 min at 37° C. Human α-CGRP is added to the cells at a concentration of 0.3 nM and allowed to incubate at 37° C. for 5 min. After α-CGRP stimulation the cells are washed with PBS and processed for cAMP determination utilizing the two-stage assay procedure according to the manufacturer's recommended protocol (cAMP SPA direct screening assay system; RPA 559; GE Healthcare). Dose response curves are plotted and $IC_{50}$ values determined from a 4-parameter logistic fit as defined by the equation y=((a−d)/(1+(x/c)^b)+d, where y=response, x=dose, a=max response, d=min response, c=inflection point and b=slope, The following abbreviations are used throughout the text:

| | |
|---|---|
| Me: | methyl |
| Et: | ethyl |
| t-Bu: | tert-butyl |
| Ar: | aryl |
| Ph: | phenyl |
| Bn: | benzyl |
| Ac: | acetylate |
| OAc: | acetate |
| BOC: | t-butyloxycarbonyl |
| BOP: | Benzotriazole-1-yl-oxy-tris-(dimethylamino)-phosphonium hexafluorophosphate |
| DIEA: | N,N-Diisopropyl-ethylamine |
| HOBT: | 1-Hydroxybenzotriazole |
| EDC: | 1-Ethyl-3-(3-dimethyllaminopropyl)carbodiimide |
| NaOt-Bu: | sodium tert-butoxide |
| HATU: | 2-(1H-7-Azabenzotriazol-1-yl)--1,1,3,3-tetramethyl uronium hexafluorophosphate Methanaminium |
| PyCIU: | 1-(Chloro-1-pyrrolidinylmethylene)pyrrolidiniumhexafluorophosphate |
| TsOH: | p-toluenesulfonic acid |
| Dba: | dibenzylideneacetone |

| | |
|---|---|
| EDTA: | Ethylenediaminetetracetic acid |
| DAST: | diethylaminosulfur trifluoride |
| BINAP: | 2,2'-bis(diphenyl phosphino)-1,1'-binaphthyl |
| DMF: | dimethylformamide |
| HMDS: | hexamethyldisilazane |
| THF: | tetrahydrofuran |
| DMSO: | dimethylsulfoxide |
| DMEM: | Dulbecco's Modified Eagle Medium (High Glucose) |
| FBS: | fetal bovine serum |
| BSA: | bovine serum albumin |
| PBS: | phosphate-buffered saline |
| HEPES: | N-(2-Hydroxyethyl)piperazine-N'-2-ethanesulfonic Acid |
| rt: | room temperature |
| h: | hours |
| aq: | aqueous |
| HPLC: | high performance liquid chromatography |
| LCMS: | liquid chromatography-mass spectrometry |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I:

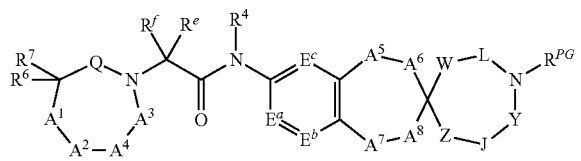

I wherein:
A$^1$ is selected from:
 (1) —O—,
 (2) —S(O)$_v$—,
 (5) —CR$^6$R$^7$—, and
 (6) —N(R$^8$)—
A$^2$ is selected from:
 (1) —CR$^6$R$^7$—,
 (2) —CR$^{10}$R$^{11}$—, and
 (3) —(C=O)—;
A$^3$ is selected from:
 (1) —CR$^6$R$^7$—,
 (2) —N(R$^8$)—,
 (3) —CR$^{10}$R$^{11}$—, and
 (4) —N(R$^{11}$)—;

A$^4$ is selected from:
 (1) —CR$^6$R$^7$—,
 (2) —(C=O)—,
 (3) —N(R$^8$)—,
 (4) —CR$^{10}$R$^{11}$—,
 (5) —N(R$^{11}$)—, and
 (6) a bond between A$^2$ and A$^3$;
A$^5$ and A$^7$ are each independently a bond;
A$^6$ and A$^8$ are each independently CH$_2$—;
E$^a$ is —C(R$^5$)=,
E$^b$ is —C(R$^5$)=,
E$^c$ is selected from:
 (1) —C(R$^5$)=
L is selected from:
 (1) —C(=O)—,
 (2) —C(=S)— and
 (5) —CR$^g$R$^h$—;
Q is
 (1) —(C=O)—;
R$^4$ is selected from:
 (1) hydrogen,
 (2) —C$_{1-6}$alkyl, which is unsubstituted or substituted with 1-5 substituents each independently selected from:
  (a) halo,
  (b) —C$_{3-6}$cycloalkyl,
  (c) —CF$_3$, and
  (d) —O—R$^a$,
 (3) —C$_{3-6}$cycloalkyl,
 (4) benzyl, and
 (5) phenyl;
R$^5$ is selected from:
 (1) hydrogen,
 (2) —C$_{1-6}$alkyl, which is unsubstituted or substituted with 1-6 halo,
 (3) halo,
 (4) —OR$^a$, and
 (5) —CN;
R$^6$ and R$^7$ are each independently selected from:
 (1) hydrogen,
 (2) —C$_{1-6}$alkyl, which is unsubstituted or substituted with 1-5 substituents each independently selected from:
  (a) halo,
  (b) —OR$^a$,
  (c) —C$_{3-6}$cycloalkyl,
  (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl, indolyl, indazolyl, benzimidazolyl, and oxazolyl, which phenyl or heterocycle is unsubstituted or substituted with 1-5 substituents each independently selected from:
   (i) halo,
   (ii) —C$_{1-6}$alkyl, which is unsubstituted or substituted with 1-5 halo,
   (iii) —OR$^a$,
   (iv) —NR$^b$R$^c$,
   (v) —CN, and
   (vi) oxo;
  (a) —CO$_2$R$^a$,
  (b) —C(=O)NR$^b$R$^c$,
  (c) —S(O)$_v$R$^d$,
  (d) —CN,
  (e) —NR$^b$R$^c$, (f) —N($R^b$)C(=O)$R^a$,
(g) —N($R^b$)$SO_2R^d$,
(h) —$CF_3$,
(i) —O—$CO_2R^d$,
(j) —O—(C=O)—N$R^b R^c$,
(k) —N$R^b$—(C=O)—N$R^b R^c$, and
(l) —C(=O)$R^a$,
(3) —$C_{3-8}$cycloalkyl, which is unsubstituted or substituted with 1-5 substituents each independently selected from:
(a) halo,
(b) —CN,
(c) —$C_{1-4}$-alkyl, which is unsubstituted or substituted with 1-3 halo, and
(d) —$OR^a$,
(4) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
(a) halo,
(b) —$OR^a$,
(c) —$C_{3-6}$cycloalkyl,
(d) phenyl, which is unsubstituted or substituted with 1-5 substituents each independently selected from:
(i) halo,
(ii) —$C_{1-6}$alkyl, which is unsubstituted or substituted with 1-6 halo, and
(iii) —$OR^a$,
(e) —$CO_2R^a$,
(f) —C(=O)N$R^b R^c$,
(g) —S(O)$_v R^d$,
(h) —CN,
(i) —N$R^b R^c$,
(j) —N($R^b$)C(=O)$R^a$,
(k) —N($R^b$)$SO_2R^d$,
(l) —O—$CO_2R^d$,
(m) —O—(C=O)—N$R^b R^c$,
(n) —N$R^b$—(C=O)—N$R^b R^c$,
(o) —C(=O)$R^a$,
(p) —$C_{1-6}$alkyl, which is unsubstituted or substituted with 1-6 halo, and oxo;
(5) halo,
(6) —$OR^a$,
(7) —CN,
(8) —$CO_2R^a$,
(9) —N($R^b$)C(=O)$R^a$,
(10) —N$R^b R^c$,
(11) —C(=O)N$R^b R^c$, and
(12) —O(C=O)$R^a$,
or $R^6$ and $R^7$ and the carbon atom to which they are attached join to form a ring selected from cyclopropyl, cyclobutyl, cyclopentyl, cyclohexyl, cycloheptyl, cyclooctyl, cyclononyl, cyclobutenyl, cyclopentenyl, cyclohexenyl, cycloheptenyl, cyclooctenyl, dioxolanyl, dioxanyl, indanyl, aziridinyl, azetidinyl, pyrrolidinyl, piperidinyl, piperazinyl, morpholinyl, tetrahydrofuranyl, tetrahydropyranyl, tetrahydrothiapyranyl, oxetanyl, thietanyl and tetrahydrothienyl, wherein the sulfur is optionally oxidized to the sulfone or sulfoxide, which ring is unsubstituted or substituted with 1-5 substituents each independently selected from:

(a) —$C_{1-6}$alkyl, which is unsubstituted or substituted with 1-3 substituents each independently selected from:
(i) halo,
(ii) —$OR^a$,
(iii) —$C_{3-6}$cycloalkyl,
(iv) —$CO_2R^a$,
(v) —N$R^b R^c$,
(vi) —S(O)$_v R^d$,
(vii) —C(=O)N$R^b R^c$, and
(viii) phenyl,
(b) —$C_{3-6}$cycloalkyl, wherein the $C_{3-6}$cycloalkyl group is optionally fused to the ring, and which $C_{3-6}$cycloalkyl group is unsubstituted or substituted with 1-3 substituents each independently selected from:
(i) halo,
(ii) —$OR^a$,
(iii) —$C_{3-6}$cycloalkyl,
(iv) —$CO_2R^a$,
(v) —N$R^b R^c$,
(vi) —S(O)$_v R^d$,
(vii) —C(=O)N$R^b R^c$, and
(viii) phenyl,
(c) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, imidazolyl, furanyl, tetrahydrofuranyl, thiazolyl and oxazolyl, wherein the phenyl or heterocycle is optionally fused to the ring, and which phenyl or heterocycle is unsubstituted or substituted with 1-5 substituents each independently selected from:
(i) halo,
(ii) —$C_{1-6}$alkyl, which is unsubstituted or substituted with 1-5 halo,
(iii) —$OR^a$,
(iv) —$CO_2R^a$,
(v) —O(C=O)$R^a$,
(vi) —CN,
(vii) —N$R^b R^c$,
(viii) oxo,
(ix) —C(=O)N$R^b R^c$,
(x) —N($R^b$)C(=O)$R^a$,
(xi) —N($R^b$)$CO_2R^a$,
(xii) —O(C=O)N$R^b R^c$, and
(xiii) —S(O)$_v R^d$,
(d) —$OR^a$,
(e) —$CO_2R^a$,
(f) —C(=O)N$R^b R^c$,
(g) —S(O)$_v R^d$,
(h) —CN,
(i) halo,
(j) —N$R^b R^c$,
(k) —N($R^b$)C(=O)$R^a$,
(l) —N($R^b$)$SO_2R^d$,
(m) —O—$CO_2R^d$,
(n) —O—(C=O)—N$R^b R^c$,
(o) —N$R^b$—(C=O)—N$R^b R^c$,
(p) —C(=O)$R^a$, and
(q) oxo;
$R^8$ is independently selected from:
(1) hydrogen,
(2) —C(=O)$R^a$,
(3) —$CO_2R^a$,
(4) —S(=O)$R^d$,
(5) —$SO_2R^d$, (6) —C(=O)NR$^b$R$^c$,
(7) —C$_{1-6}$alkyl, which is unsubstituted or substituted with 1-5 substituents each independently selected from:
  (a) halo,
  (b) —OR$^a$,
  (c) —C$_{3-6}$cycloalkyl,
  (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
    (i) halo,
    (ii) —C$_{1-6}$alkyl, which is unsubstituted or substituted with 1-5 halo, and
    (iii) —OR$^a$,
    (iv) —NR$^b$R$^c$,
    (v) —C(=O)R$^a$,
    (vi) —CO$_2$R$^a$, and
    (vii) oxo,
  (e) —CO$_2$R$^a$,
  (f) —C(=O)NR$^b$R$^c$,
  (g) —S(O)$_v$R$^d$,
  (h) —CN,
  (i) —NR$^b$R$^c$,
  (j) —N(R$^b$)C(=O)R$^a$,
  (k) —N(R$^b$)SO$_2$R$^d$,
  (l) —CF$_3$,
  (m) —O—CO$_2$R$^d$,
  (n) —O—(C=O)—NR$^b$R$^c$,
  (o) —NR$^b$—(C=O)—NR$^b$R$^c$, and
  (p) —C(=O)R$^a$,
(8) —C$_{3-6}$cycloalkyl, which is unsubstituted or substituted with 1-6 substituents each independently selected from:
  (a) halo,
  (b) —CN,
  (c) —OR$^a$, and
  (d) C$_{1-6}$alkyl, which is unsubstituted or substituted with 1-6 halo,
or R$^7$ and R$^8$ and the atoms to which they are attached join to form a 4-, 5-, 6- or 7-membered alkyl- or heteroalkyl-ring optionally containing an additional heteroatom selected from N, O, and S, wherein the sulfur is optionally oxidized to the sulfone or sulfoxide, which ring is unsubstituted or substituted with 1-4 substituents each independently selected from:
  (a) halo,
  (b) phenyl, which is unsubstituted or substituted with 1-3 substituents each independently selected from: halo, OR$^a$, CN, and —C(=O)OR$^a$,
  (c) —OR$^a$, and
  (d) —C$_{1-6}$alkyl, which is unsubstituted or substituted with 1-6 halo;
R$^{10}$ is independently selected from:
(1) hydrogen,
(2) —C$_{1-6}$alkyl, which is unsubstituted or substituted with 1-5 substituents each independently selected from:
  (a) halo,
  (b) —OR$^a$,
  (c) —CN,
  (d) phenyl, and
  (e) —C$_{3-6}$cycloalkyl, which is unsubstituted or substituted with 1-6 halo,
(3) —C$_{3-6}$cycloalkyl, which is unsubstituted or substituted with 1-6 halo;
R$^{11}$ is independently selected from the group consisting of:
  phenyl, naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, 1,3-benzodioxolyl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiapyranyl, and thietanyl, where R$^{11}$ is unsubstituted or substituted with 1-5 substituents each independently selected from R$^{12}$, R$^{13}$, R$^{14}$, R$^{15a}$ and R$^{15b}$;
R$^{12}$, R$^{13}$, R$^{14}$, R$^{15a}$ and R$^{15b}$ are each independently selected from:
(1) —C$_{1-6}$alkyl, which is unsubstituted or substituted with 1-5 substituents each independently selected from:
  (a) halo,
  (b) —OR$^a$,
  (c) —C$_{3-6}$cycloalkyl,
  (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
    (i) halo,
    (ii) —C$_{1-6}$alkyl, which is unsubstituted or substituted with 1-5 halo, and
    (iii) —OR$^a$,
  (e) —CO$_2$R$^a$,
  (f) —C(=O)NR$^b$R$^c$,
  (g) —S(O)$_v$R$^d$,
  (h) —CN,
  (i) —NR$^b$R$^c$,
  (j) —N(R$^b$)C(=O)R$^a$,
  (k) —N(R$^b$)SO$_2$R$^d$,
  (l) —CF$_3$,
  (m) —O—CO$_2$R$^d$,
  (n) —O—(C=O)—NR$^b$R$^c$,
  (o) —NR$^b$—(C=O)—NR$^b$R$^c$, and
  (p) —C(=O)R$^a$, (2) —$C_{1-6}$cycloalkyl, which is unsubstituted or substituted with 1-5 substituents each independently selected from:
  (a) halo,
  (b) —CN,
  (c) —$C_{1-6}$alkyl, which is unsubstituted or substituted with 1-5 halo,
  (d) —$OR^a$, and
  (e) phenyl, which is unsubstituted or substituted with 1-5 substituents where the substituents are each independently selected from:
    (i) —$OR^a$,
    (ii) halo,
    (iii) —CN, and
    (iv) —$C_{1-6}$alkyl, which is unsubstituted or substituted with 1-5 halo,
(3) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
  (a) halo,
  (b) —$OR^a$,
  (c) —$C_{3-6}$cycloalkyl,
  (d) phenyl, which is unsubstituted or substituted with 1-5 substituents each independently selected from:
    (i) halo,
    (ii) —$C_{1-6}$alkyl, which is unsubstituted or substituted with 1-6 halo, and
    (iii) —$OR^a$,
  (e) —$CO_2R^a$,
  (f) —$C(=O)NR^bR^c$,
  (g) —$S(O)_vR^d$,
  (h) —CN,
  (i) —$NR^bR^c$,
  (j) —$N(R^b)C(=O)R^a$,
  (k) —$N(R^b)SO_2R^d$,
  (l) —O—$CO_2R^d$,
  (m) —O—(C=O)—$NR^bR^c$,
  (n) —$NR^b$—(C=O)—$NR^bR^c$,
  (o) —$C(=O)R^a$, and
  (p) —$C_{1-6}$alkyl, which is unsubstituted or substituted with 1-6 halo,
(4) halo,
(5) oxo,
(6) —$OR^a$,
(7) —CN,
(8) —$CO_2R^a$,
(9) —$C(=O)R^a$,
(10) —$NR^bR^c$,
(11) —$S(O)_vR^d$,
(12) —$C(=O)NR^bR^c$,
(13) —O—$CO_2R^d$,
(14) —$N(R^b)CO_2R^d$,
(15) —O—(C=O)—$NR^bR^c$,
(16) —$NR^b$—(C=O)—$NR^bR^c$,
(17) —$SO_2NR^bR^c$,
(18) —$N(R^b)SO_2R^d$,
or $R^{15a}$ and $R^{15b}$ and the atom(s) to which they are attached join to form a ring selected from cyclopropyl, cyclobutyl, cyclopentyl, cyclohexyl, cycloheptyl, aziridinyl, azetidinyl, pyrrolidinyl, piperidinyl, piperazinyl, morpholinyl, thietanyl and tetrahydrothienyl, wherein the sulfur is optionally oxidized to the sulfone or sulfoxide, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) —$OR^a$,
    (iii) —$C_{3-6}$cycloalkyl,
    (iv) —$CO_2R^a$,
    (v) —$NR^bR^c$,
    (vi) —$S(O)_vR^d$,
    (vii) —$C(=O)NR^bR^c$, and
    (viii) phenyl,
  (b) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
    (i) halo,
    (ii) —$C_{1-6}$alkyl, which is unsubstituted or substituted with 1-5 halo, and
    (iii) —$OR^a$,
  (c) —$OR^a$,
  (d) halo,
  (e) —$CO_2R^a$,
  (f) —$C(=O)NR^bR^c$,
  (g) —$S(O)_vR^d$,
  (h) —CN,
  (i) —$NR^bR^c$,
  (j) —$N(R^b)C(=O)R^a$,
  (k) —$N(R^b)SO_2R^d$,
  (l) —O—$CO_2R^d$,
  (m) —O—(C=O)—$NR^bR^c$,
  (n) —$NR^b$—(C=O)—$NR^bR^c$, and
  (o) —$C(=O)R^a$;
$R^{PG}$ is independently selected from:
  (1) hydrogen, and
  (2) —$C_{1-6}$alkyl which is unsubstituted or substituted with 1-5 halo
J is independently selected from:
  (1) =$C(R^{16a})$—, and
  (2) —$CR^{17}R^{18}$;
Y is independently selected from:
  (1) =$C(R^{16b})$—, and
  (2) —$CR^{17}R^{18}$;
W is
  O—;
Z is
  a bond,
$R^{17}$ and $R^{18}$ are each independently selected from:
  (1) hydrogen,
  (2) halo,
  (3) —$OR^a$,
  (4) —$C_{1-6}$alkyl, which is unsubstituted or substituted with 1-4 substituents each independently selected from:
    (a) halo,
    (b) —$OR^a$,
    (c) —CN,
    (d) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
(i) —OR$^a$,
(ii) halo,
(iii) —CN,
(iv) —C$_{1-6}$alkyl which is unsubstituted or substituted with 1-6 halo,
(5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
(a) halo,
(b) —CN,
(c) —OR$^a$,
(d) nitro,
(e) —C$_{1-6}$alkyl which is unsubstituted or substituted with 1-6 halo,
or R$^{17}$ and R$^{18}$ and the atom to which they are attached join to form a 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
(a) halo,
(b) —OR$^a$,
(c) —C$_{1-6}$alkyl, which is unsubstituted or substituted with 1-6 halo, and
(d) phenyl;
R$^{16a}$ and R$^{16b}$ are each independently selected from:
(1) hydrogen,
(2) —C$_{1-4}$-alkyl, which is unsubstituted or substituted with 1-5 substituents each independently selected from:
(a) halo,
(b) —OR$^a$,
(c) —C$_{3-6}$cycloalkyl,
(d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is unsubstituted or substituted with 1-3 substituents each independently selected from:
(i) halo,
(ii) —OR$^a$,
(iii) —CN, and
(iv) C$_{1-6}$alkyl, which is unsubstituted or substituted with 1-6 halo,
(3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is unsubstituted or substituted with 1-3 substituents each independently selected from:
(a) halo,
(b) —OR$^a$,
(c) —C$_{3-6}$cycloalkyl,
(d) —C$_{1-4}$-alkyl which is unsubstituted or substituted with 1-6 halo, and
(e) phenyl, which is unsubstituted or substituted with 1-5 substituents each independently selected from:
(i) halo,
(ii) —C$_{1-6}$alkyl, which is unsubstituted or substituted with 1-6 halo, and
(iii) —OR$^a$,
(4) halo,
(5) —OR$^a$,
(6) —CN,
(7) —CO$_2$R$^a$,
(8) —NR$^b$R$^c$,
(9) —C(=O)NR$^b$R$^c$, and
(10) —C$_{3-6}$cycloalkyl which is unsubstituted or substituted with 1-6 halo,
or R$^{16a}$ and R$^{16b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
(a) —C$_{1-6}$alkyl, which is unsubstituted or substituted with 1-3 substituents each independently selected from:
(i) halo,
(ii) —OR$^a$,
(iii) —C$_{3-6}$cycloalkyl,
(iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
(I) —OR$^a$,
(II) halo,
(III) —CN, and
(IV) —C$_{1-6}$alkyl which is unsubstituted or substituted with 1-6 halo,
(v) —CO$_2$R$^a$,
(vi) —NR$^b$R$^c$,
(vii) —S(O)$_v$R$^d$,
(viii) —C(=O)NR$^b$R$^c$,
(ix) —N(R$^b$)CO$_2$R$^a$, and
(x) —N(R$^b$)SO$_2$R$^d$,
(b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-5 substituents each independently selected from:
(i) halo,
(ii) —OR$^a$,
(iii) —CN, and
(iv) —C$_{1-6}$alkyl which is unsubstituted or substituted with 1-6 halo,
(c) halo,
(d) —S(O)$_v$R$^d$,
(e) —OR$^a$,
(f) —CN,
(g) —C(=O)R$^a$,
(h) —NR$^b$R$^c$,
(i) —C(=O)NR$^b$R$^c$,
(j) —CO$_2$R$^a$, (k) —(NR$^b$)CO$_2$R$^a$,
(l) —O—(C=O)—NR$^b$R$^c$,
(m) —(NR$^b$)—(C=O)—NR$^b$R$^c$,
(n) oxido,
(o) oxo, and
(p) —(NR$^b$)SO$_2$R$^d$;

R$^a$ is independently selected from:
(1) hydrogen,
(2) C$_{1-6}$alkyl, which is unsubstituted or substituted with 1-7 substituents each independently selected from:
  (a) halo,
  (b) —O—C$_{1-6}$alkyl, which is unsubstituted or substituted with 1-6 halo,
  (c) hydroxyl,
  (d) —CN, and
  (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    i) halo,
    ii) —O—C$_{1-6}$alkyl, which is unsubstituted or substituted with 1-6 halo,
    iii) —CN,
    iv) nitro,
    v) hydroxyl, and
    vi) —C$_{1-6}$alkyl, which is unsubstituted or substituted with 1-6 halo,
(3) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (a) halo,
  (b) —CN,
  (c) —O—C$_{1-6}$alkyl, which is unsubstituted or substituted with 1-6 halo,
  (d) nitro,
  (e) hydroxyl, and
  (f) —C$_{1-6}$alkyl, which is unsubstituted or substituted with 1-6 halo, and
(4) —C$_{3-6}$cycloalkyl, which is unsubstituted or substituted with 1-6 halo;

R$^b$ and R$^c$ are independently selected from:
(1) hydrogen,
(2) C$_{1-6}$alkyl, which is unsubstituted or substituted with 1-7 substituents each independently selected from:
  (a) halo,
  (b) —OR$^a$,
  (c) —CN,
  (d) —CO$_2$R$^a$,
  (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —OR$^a$,
    (iii) —C$_{1-6}$alkyl, which is unsubstituted or substituted with 1-6 halo, and
    (iv) nitro,
(3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (a) halo,
  (b) —OR$^a$,
  (c) —C$_{1-6}$alkyl, which is unsubstituted or substituted with 1-6 halo,
  (d) —C$_{3-6}$cycloalkyl, which is unsubstituted or substituted with 1-6 halo,
  (e) —CN, and
  (f) —CO$_2$R$^a$,
(4) —C$_{3-6}$cycloalkyl, which is unsubstituted or substituted with 1-6 halo,
or R$^b$ and R$^c$ and the nitrogen to which they are attached join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from:
  (a) halo,
  (b) —OR$^a$, and
  (c) —C$_{1-6}$alkyl, which is unsubstituted or substituted with 1-6 halo, and
  (d) phenyl;

R$^d$ is independently selected from:
(1) C$_{1-6}$alkyl, which is unsubstituted or substituted with 1-4 substituents each independently selected from:
  (a) halo,
  (b) —OR$^a$,
  (c) —CO$_2$R$^a$,
  (d) —CN, and
  (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —OR$^a$,
    (iii) —C$_{1-6}$alkyl, which is unsubstituted or substituted with 1-6 halo, and
    (iv) nitro,
(2) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (a) halo,
  (b) —OR$^a$,
  (c) —C$_{1-6}$alkyl, which is unsubstituted or substituted with 1-6 halo,
  (d) —C$_{3-6}$cycloalkyl, which is unsubstituted or substituted with 1-6 halo
  (e) —CN, and
  (f) —CO$_2$R$^a$, and
(3) —C$_{3-6}$cycloalkyl, which is unsubstituted or substituted with 1-6 halo;

$R^e$ and $R^f$ are independently selected from:
(1) hydrogen,
(2) —$C_{1-4}$-alkyl, which is unsubstituted or substituted with 1-6 halo,
(3) phenyl, and
(4) benzyl;
or where $R^e$ and $R^f$ and the atom to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
(a) halo,
(b) —$OR^a$,
(c) —$C_{1-6}$alkyl, which is unsubstituted or substituted with 1-6 halo, and
(d) phenyl;

$R^g$ and $R^h$ are independently selected from:
(1) hydrogen,
(2) halo,
(3) —$C_{1-4}$-alkyl, which is unsubstituted or substituted with 1-6 halo,
(4) phenyl, and
(5) benzyl;
or where $R^g$ and $R^h$ and the atom to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
(a) halo,
(b) —$OR^a$,
(c) —$C_{1-6}$alkyl, which is unsubstituted or substituted with 1-6 halo, and
(d) phenyl;

v is 0, 1, or 2;
or a pharmaceutically acceptable salt thereof, and individual enantiomers and diastereomers thereof.

2. A compound of claim 1, wherein $A^1$ is —$N(R^8)$—, and $R^8$ is hydrogen or —$C_{1-3}$alkyl.

3. A compound of claim 1, or a pharmaceutically acceptable salt thereof, wherein $A^2$ is selected from:
(1) —$CR^6R^7$—, or
(2) —$CR^{10}R^{11}$—.

4. A compound of claim 1, or a pharmaceutically acceptable salt thereof, wherein $A^3$ is selected from:
(1) —$CR^6R^7$—, or
(2) —$CR^{10}R^{11}$—.

5. A compound of claim 1, or a pharmaceutically acceptable salt thereof, wherein $A^4$ is selected from:
(1) —$CR^6R^7$—,
(2) —$CR^{10}R^{11}$—, or
(3) a bond.

6. A compound of claim 1, or a pharmaceutically acceptable salt thereof, wherein $R^4$ is selected from:
(1) hydrogen, or
(2) —$C_{1-6}$alkyl, which is unsubstituted or substituted with 1-5 substituents each independently selected from:
(a) halo,
(b) —$C_{3-6}$cycloalkyl,
(c) —$CF_3$, and
(d) —O—$R^a$.

7. A compound of claim 1, or a pharmaceutically acceptable salt thereof, wherein J is =$C(R^{16a})$—, and Y is =$C(R^{16b})$—, and
$R^{16a}$ and $R^{16b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl.

8. A compound of claim 1, or a pharmaceutically acceptable salt thereof, wherein $R^e$ and $R^f$ are independently selected from:
(1) hydrogen,
(2) —$C_{1-4}$alkyl, which is unsubstituted or substituted with 1-6 halo,
or $R^e$ and $R^f$ and the atom to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
(a) halo,
(b) —$OR^a$,
(c) —$C_{1-6}$alkyl, which is unsubstituted or substituted with 1-6 halo, and
(d) phenyl.

9. A compound of claim 1 which is selected from the group consisting of
2-(3,4-dimethyl-2-oxo-6-phenylpiperazin-1-yl)-N-(2'-oxo-1,1',2',3-tetrahydrospiro[indene-2,4'-pyrido[2,3-d][1,3]oxazin]-5-yl)acetamide;
or a pharmaceutically acceptable salt thereof.

10. A pharmaceutical composition which comprises an inert carrier and the compound of claim 1, or a pharmaceutically acceptable salt thereof.

* * * * *